(12) United States Patent
Mathonneau et al.

(10) Patent No.: US 7,815,901 B2
(45) Date of Patent: Oct. 19, 2010

(54) HAIR TREATMENT METHOD

(75) Inventors: Estelle Mathonneau, Paris (FR); Isabelle Rollat-Corvol, Paris (FR); Henri Samain, Bievres (FR)

(73) Assignee: L'Oréal S.A., Paris (FR)

( * ) Notice: Subject to any disclaimer, the term of this patent is extended or adjusted under 35 U.S.C. 154(b) by 1150 days.

(21) Appl. No.: 11/340,654

(22) Filed: Jan. 27, 2006

(65) Prior Publication Data

US 2007/0020215 A1 Jan. 25, 2007

Related U.S. Application Data

(60) Provisional application No. 60/727,448, filed on Oct. 18, 2005.

(30) Foreign Application Priority Data

Jan. 28, 2005 (FR) .................................. 05 50249

(51) Int. Cl.
A61Q 5/04 (2006.01)
(52) U.S. Cl. ...................... 424/70.2; 132/207
(58) Field of Classification Search ........................ None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,579,629 A | 5/1971 | Pasero et al. | |
| 3,716,633 A | 2/1973 | Viout et al. | |
| 3,810,977 A | 5/1974 | Levine et al. | |
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,070,533 A | 1/1978 | Papantoniou et al. | |
| 4,076,912 A | 2/1978 | Papantoniou et al. | |
| 4,103,145 A | 7/1978 | Oliveri | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,693,935 A | 9/1987 | Mazurek | |
| 4,728,571 A | 3/1988 | Clemens et al. | |
| 4,956,175 A | 9/1990 | Maignan et al. | |
| 4,972,037 A | 11/1990 | Garbe et al. | |
| 5,015,767 A | 5/1991 | Maignan et al. | |
| 5,085,860 A | 2/1992 | Jumino et al. | |
| 5,106,612 A | 4/1992 | Maignan et al. | |
| 5,154,918 A * | 10/1992 | Maignan et al. ........... 424/70.51 |
| 5,334,377 A | 8/1994 | Junino et al. | |
| 5,449,805 A | 9/1995 | Junino et al. | |
| 5,466,878 A | 11/1995 | Junino et al. | |
| 5,538,717 A | 7/1996 | de La Poterie | |
| 5,570,708 A * | 11/1996 | Samain ....................... 132/205 |
| 5,583,257 A | 12/1996 | Junino et al. | |
| 5,700,454 A | 12/1997 | Malle | |
| 5,843,416 A | 12/1998 | Malle | |
| 5,899,213 A | 5/1999 | Kimata | |
| 5,935,558 A | 8/1999 | Malle | |
| 5,957,140 A | 9/1999 | McGee | |
| 5,983,903 A | 11/1999 | Namba et al. | |
| 5,985,257 A | 11/1999 | Malle | |
| 6,106,813 A | 8/2000 | Mondet et al. | |
| 6,166,093 A | 12/2000 | Mougin et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,471,953 B1 | 10/2002 | N'Guyen et al. | |
| 6,770,271 B2 | 8/2004 | Mondet et al. | |
| 2002/0150546 A1 | 10/2002 | Mougin et al. | |
| 2005/0002886 A1 | 1/2005 | Philippe et al. | |
| 2005/0039270 A1 | 2/2005 | Legrand et al. | |

(Continued)

FOREIGN PATENT DOCUMENTS

DE 23 30 956 B1 1/1974

(Continued)

OTHER PUBLICATIONS

French Search Report for FR 05/50249, Sep. 9, 2005.

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

Disclosed herein is a method for treating keratinous fibers comprising coating the keratinous fibers with a reducing agent, rinsing the keratinous fibers, coating the keratinous fibers with a cosmetic composition comprising at least one non crystalline or semi-crystalline fixing polymer, and/or at least one cerid, and/or at least one sterid, raising the temperature of the keratinous fibers, and coating the keratinous fibers with an oxidizing agent. This method may make it possible to achieve a hair style with an excellent hold which is durable over time.

23 Claims, 3 Drawing Sheets

U.S. PATENT DOCUMENTS

| | | |
|---|---|---|
| 2005/0042190 A1 | 2/2005 | Nicolas-Morgantini et al. |
| 2005/0112076 A1 | 5/2005 | Fondin et al. |
| 2006/0263316 A1* | 11/2006 | Devin-Baudoin .......... 424/70.7 |

FOREIGN PATENT DOCUMENTS

| | | |
|---|---|---|
| EP | 0 354 835 B1 | 12/1990 |
| EP | 0 412 704 B1 | 2/1991 |
| EP | 0 412 707 B1 | 2/1991 |
| EP | 0 432 000 B1 | 6/1991 |
| EP | 0 465 342 B1 | 1/1992 |
| EP | 0 514 282 B1 | 11/1992 |
| EP | 0 582 152 B1 | 2/1994 |
| EP | 0 619 111 B1 | 10/1994 |
| EP | 0 637 600 B1 | 2/1995 |
| EP | 0 648 485 B1 | 4/1995 |
| EP | 0 653 202 B1 | 5/1995 |
| EP | 0 656 021 B1 | 6/1995 |
| EP | 0 751 162 B1 | 1/1997 |
| EP | 1 064 921 B1 | 1/2001 |
| EP | 1 433 467 A1 | 6/2004 |
| EP | 1 475 074 A1 | 11/2004 |
| EP | 1 475 076 A1 | 11/2004 |
| EP | 1 486 196 A1 | 12/2004 |
| FR | 1 222 944 | 6/1960 |
| FR | 1 400 366 | 4/1965 |
| FR | 1 564 110 | 4/1969 |
| FR | 1 580 545 | 9/1969 |
| FR | 2 077 143 | 10/1971 |
| FR | 2 102 113 | 4/1972 |
| FR | 2 198 719 | 4/1974 |
| FR | 2 265 781 | 10/1975 |
| FR | 2 265 782 | 10/1975 |
| FR | 2 350 384 | 12/1977 |
| FR | 2 393 573 | 1/1979 |
| FR | 2 439 798 | 5/1980 |
| FR | 2 743 297 A1 | 7/1997 |
| GB | 839 805 | 6/1960 |
| GB | 922 457 | 4/1963 |
| GB | 1 021 400 | 3/1966 |
| GB | 1 334 416 | 10/1973 |
| GB | 1 408 388 | 10/1975 |
| WO | WO 93/23009 | 11/1993 |
| WO | WO 93/23446 | 11/1993 |
| WO | WO 94/03510 | 2/1994 |
| WO | WO 95/00578 | 1/1995 |

OTHER PUBLICATIONS

English language abstract for EP 0 080 976 B1, Jun. 8, 1983.
English language abstract for EP 0 368 763 B1, May 16, 1990.
English language abstract for FR 2 357 241, Feb. 3, 1978.
English language abstract for FR 2 679 448 A1, Jan. 29, 1993.
English language abstract for FR 2 692 481 A1, Dec. 24, 1993.

* cited by examiner

HAIR TREATMENT METHOD

This application claims benefit of U.S. Provisional Application No. 60/727,448, filed Oct. 18, 2005, the contents of which are incorporated herein by reference. This application also claims benefit of priority under 35 U.S.C. §119 to French Patent Application No. 05 50249, filed Jan. 28, 2005, the contents of which are also incorporated herein by reference.

Disclosed herein is a hair treatment method comprising successively applying to the hair at least one reducing agent, at least one rinsing material, at least one entity chosen from polymers, cerids, and sterids, at least one heat source, and at least one fixing agent.

Hair styling products making it possible to give a hair style particular original shapes may include, for example, gels, solutions, and foams containing a fixing polymer. The inconvenience associated with such a product type lies in that holding the hair in place may be limited over time, for example, the shape may be lost when the hair is being shampooed for the first time.

In addition, permanent treatments for keratin fibers are known. Such methods comprise a first step comprising the opening of disulfide links of the keratin (cystine) using a composition containing a reducing agent, and, after the hair has been optionally rinsed, recreating said disulfide links by applying on the smoothed or previously stretched hair, using appropriate means such as hair-curlers, an oxidizing composition, also referred to as fixing agent, so as to impart to the hair the desired shape. Such a technique indiscriminately may allow for the waving, straightening, backcombing, and/or smoothing of the hair.

It is desirable to provide novel compositions which allow the user to fix the hair durably in very different shapes.

The present inventor has therefore developed a method for treating keratinous fibers comprising:
coating the keratinous fibers with at least one reducing agent,
rinsing the keratinous fibers,
coating the keratinous fibers with a cosmetic composition comprising at least one non-crystalline or semi-crystalline fixing polymer, and/or at least one cerid, and/or at least one sterid,
raising the temperature of the keratinous fibers, using at least one heat source, up to a temperature ranging from 50 to 280° C., and
coating the keratinous fibers with at least one oxidizing agent.

BRIEF DESCRIPTION OF THE DRAWINGS

The accompanying drawings, which are incorporated herein and constitute a part of this specification, illustrate several embodiments of the presently disclosed invention, and together with the description, serve to explain the principles of the invention.

The heat source helps to impart the shape to the hair. The heat source may be applied to the hair by pressing the hair continuously or discontinuously.

In at least one embodiment, the heat source may be a smoothing tong, curling tong, or waving tong, allowing the user to impart original shapes to the hair locks.

The tong may allow the user to impart to the hair any pattern and/or shape type, and, for example, projecting or "curved" shapes, such as circular and elliptical shapes, for example, spots, ovals, rectangular, and hexagonal shapes, small squares, rectangles, hexagons, triangles, patterns imitating hair styles such as plaits, or any other patterns representing any object or image shape.

For "imparting" the shape or the pattern to the hair, tweezers may be pressed around a hair lock onto which the reducing agent and the cosmetic composition containing at least one non crystalline or semi-crystalline polymer, and/or at least one cerid, and/or at least one sterid have been applied.

Thus, the heating tong may comprise tweezers with two branches, the section of each branch having any shape, for example, chosen from rectangular, curved, triangular, and polyhexagonal shapes.

The branches of the tong may have symmetrical shapes or shapes complementary to each other. One branch or both branches of the tong may be capable of being heated. Non-limiting examples of branches of various heating tongs are illustrated in a sectional view in FIG. 1.

Figure 1:
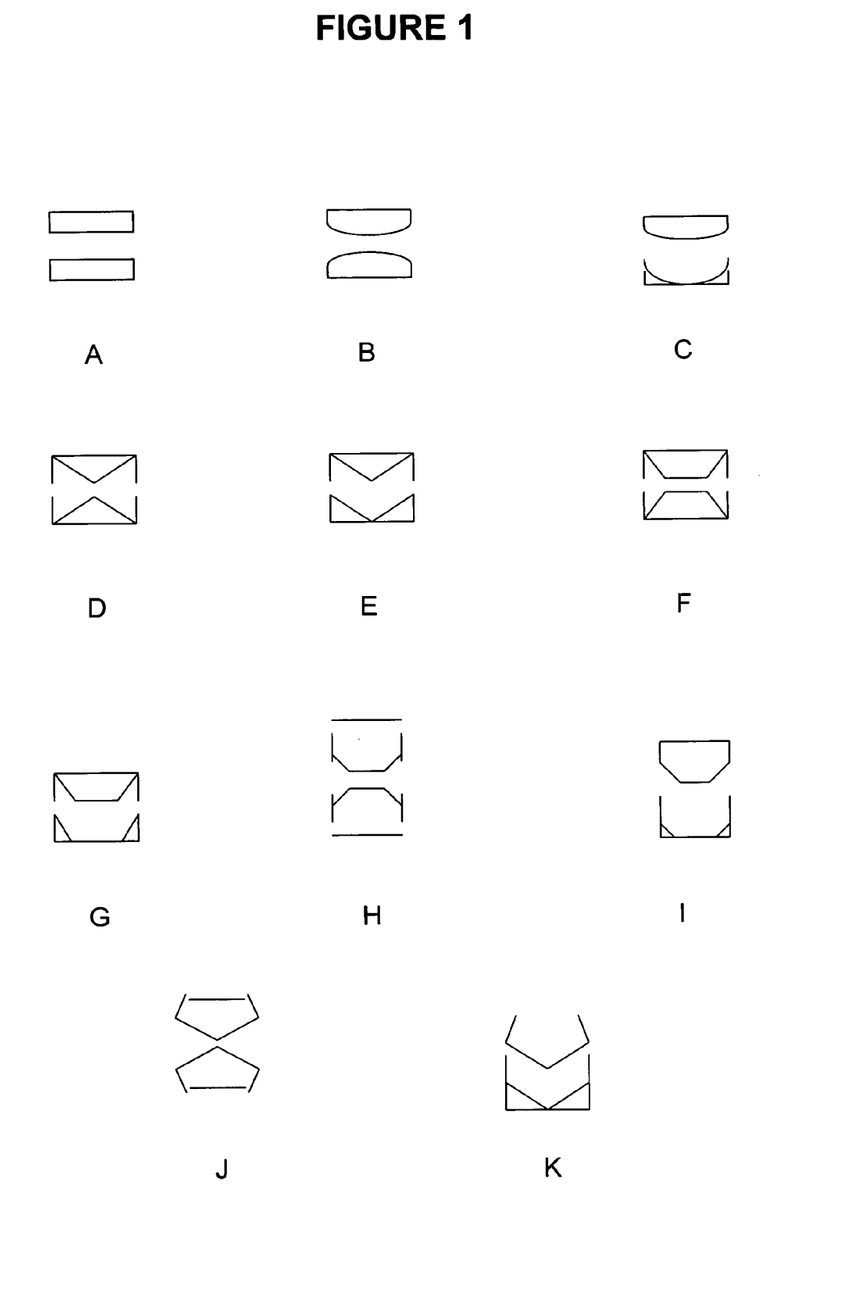
FIGS. 1A to 1K illustrate sectional views of branches of various heating tongs.

In one embodiment of the present disclosure, the branches of the tong may be flat, symmetrically curved, complementarily curved, symmetrically triangular, complementarily triangular, symmetrically polyhexagonal, or complementarily polyhexagonal.

In order to impart original shapes to the hair locks, the branches of the tong may be coated with a mold having a variable shape.

Non-limiting examples of molds able to be adapted to the surface of the branches of a tong are illustrated in FIGS. 2A, 2B, and 2C.

Figure 2:
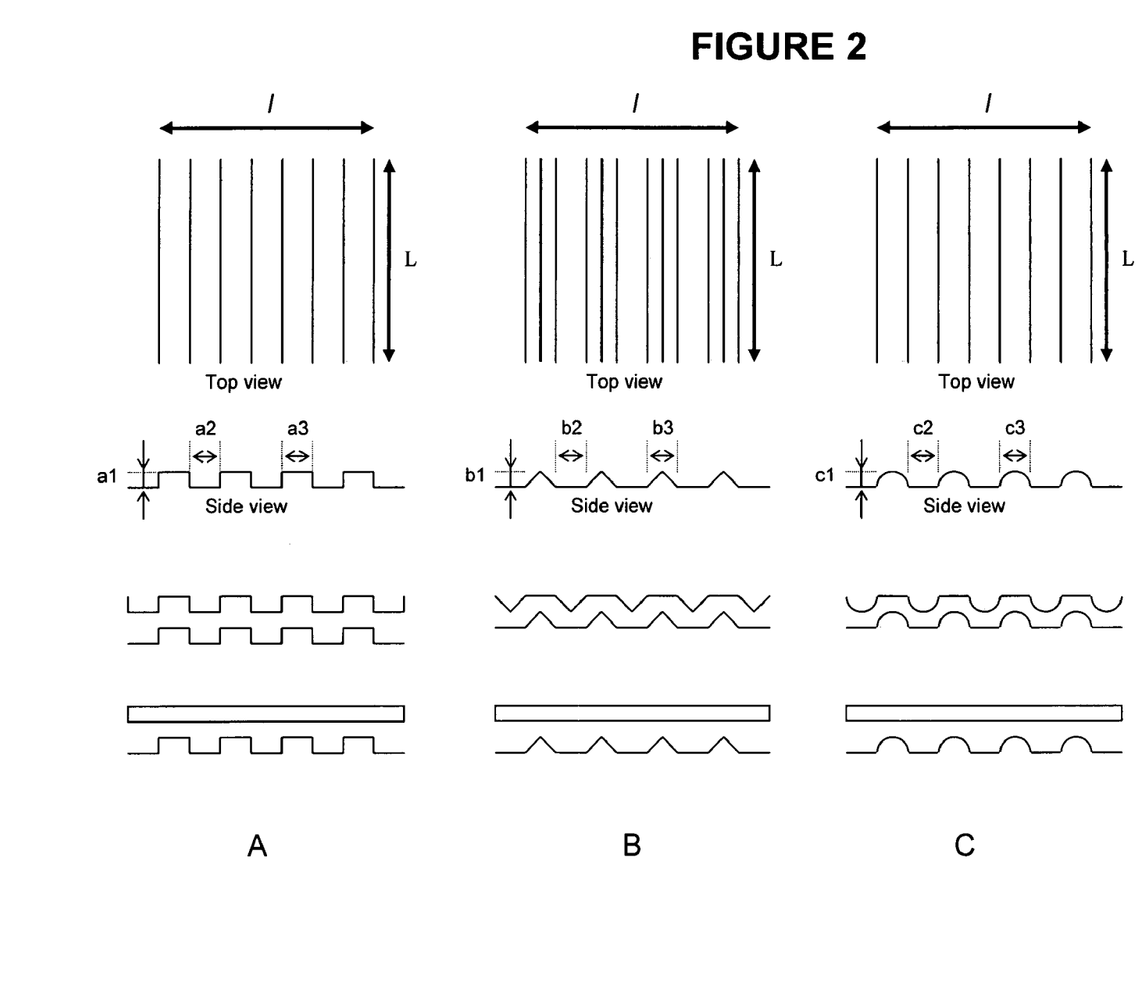
FIGS. 2A to 2C illustrate sectional and top views of molds adaptable on heating tongs.

As is illustrated in FIG. 2, the molds may have a width "I" ranging from 0.5 to 30 cm, for example, from 2 to 15 cm, a length "L" ranging from 2 to 30 cm, for example, from 5 to 15 cm. In at least one embodiment, the molds may have dimensions as shown in FIG. 2, wherein:

$a_1$, $b_1$, and $c_1$ may range from 0.1 to 5 cm, for example, from 0.1 to 1.5 cm, $a_2$, $b_2$, and $c_2$ may range from 0.1 to 10 cm, for example, from 0.5 to 5 cm, and $a_3$, $b_3$, and $c_3$ may range from 0.1 to 10 cm, for example, from 0.5 to 5 cm.

However, it is to be understood that these dimensions are merely exemplary and the molds may have any dimensions suitable for imparting shape to the hair.

Figure 3:
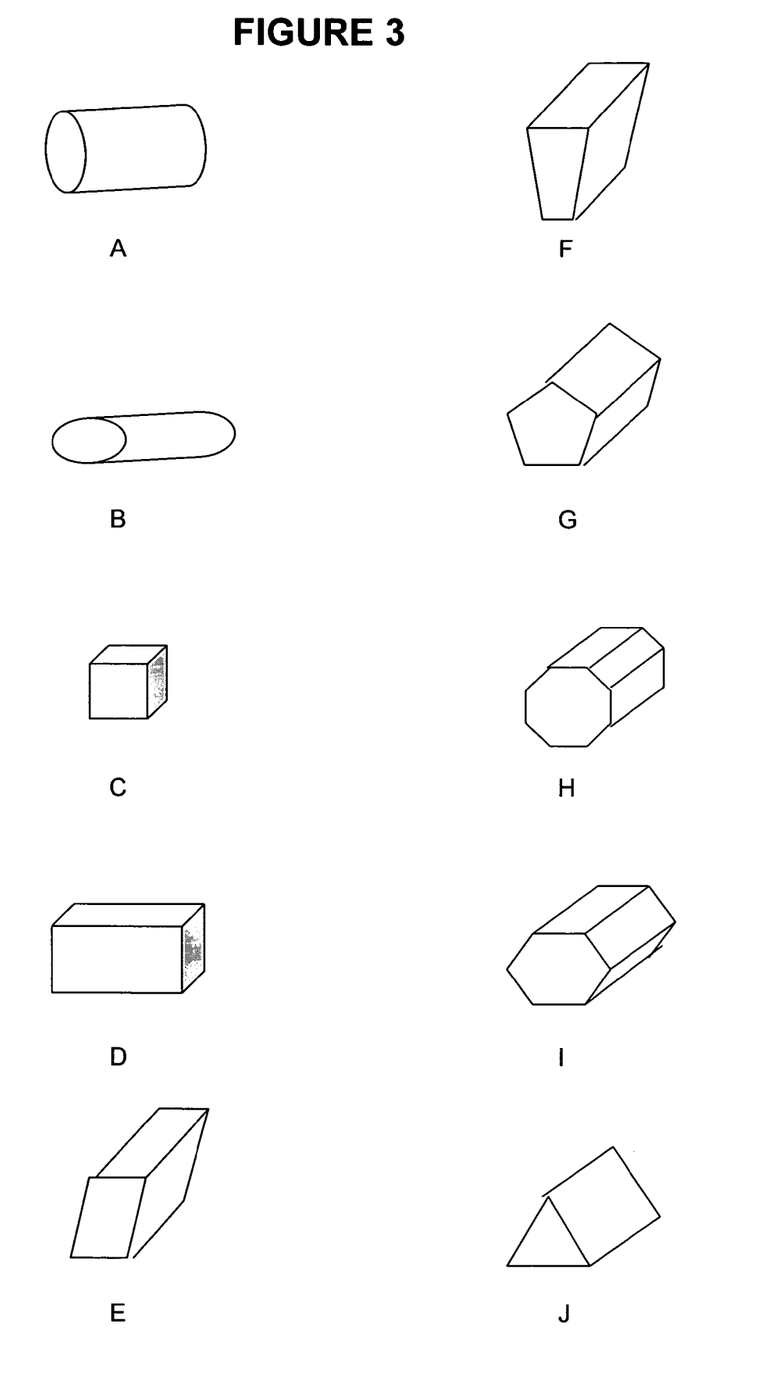
FIGS. 3A to 3J illustrate sectional view of tongs comprising a single heating element.

In another embodiment, the heat source may be a tong comprising a single heating element around which the keratinous fibers may be twisted. Such an element may have a varied shape, for example, a cylindrical or parallelepiped shape. Non-limiting examples of such heating sources are illustrated in FIG. 3.

The heat source may thus comprise one element with a section having a shape chosen from circular, oval, squared, rectangular, parallelepipedic, trapezoid, pentagonal, hexagonal, octagonal, and triangular shapes.

In at least one embodiment of the present disclosure, the step comprising coating the keratinous fibers with at least one cosmetic composition comprising at least one fixing polymer, and/or at least one cerid, and/or at least one sterid and the step comprising raising the temperature of the keratinous fibers may be carried out simultaneously.

The above embodiment may be implemented using a device comprising a heat source and a tank containing a cosmetic composition comprising at least one fixing polymer, and/or at least one cerid, and/or at least one sterid. For example, such a conditioning and application device may comprise:

a tank, either heated or not heated, containing a composition comprising at least one non crystalline or semi-crystalline polymer, and/or at least one cerid, and/or at least one sterid, a coating device, and a heating means arranged on both sides of the coating device allowing the user to heat the fibers prior to, simultaneously with, and/or after coating the fibers with the cosmetic composition (at a temperature higher than the melting point of the cosmetic composition).

The heating means may therefore serve as a coater.

The at least one reducing agent may be chosen from thiols such as thioglycolic acid, thiolactic acid, 3-mercaptopropionic acid, thiomalic acid, 2,3-dimercaptosuccinic acid, cysteine, N-glycyl-L-cysteine, and L-cysteinylglycine as well as the esters and salts thereof; thioglycerol, cysteamine, and the $C_1$-$C_4$ acylated derivates thereof; N-mesylcysteamine; N-acetylcysteine; sugar N-mercaptoalkylamides such as N-(mercapto-2-ethyl)gluconamide; pantetheine; N-(mercaptoalkyl)-ω-hydroxy alkylamides, for example, those disclosed in European Patent Application No. 0 354 835; N-mono or N,N-dialkylmercapto-4 butyramides, for example, those disclosed in European Patent Application No. 0 368 763; aminomercapto-alkylamides, for example, those disclosed in European Patent Application No. 0 432 000; derivatives of N-(mercapto-alkyl)succinamic acids and N-(mercaptoalkyl)succinimides, for example, those disclosed in European Patent Application No. 0 465 342; alkylamino mercaptoalkylamides, for example, those disclosed in European Patent Application No. 0 514 282; an azeotropic mixture of 2-hydroxypropyl thioglycolate and (2-hydroxy-1-methyl)ethyl thioglycolate, such as that disclosed in French Patent Application No. 2 679 448; mercaptoalkylaminoamides, for example, those disclosed in French Patent Application No. 2 692 481; and N-mercaptoalkylalkane diamides, for example, those disclosed in European Patent Application No. 0 653 202.

The reducing agent may also be chosen from hydrides such as sodium borohydride, potassium borohydride, sulfites of alkali earth metals, sulfites of alkaline earth metals, bisulfites of alkali earth metals, bisulfites of alkaline earth metals, and phosphorus derivatives, such as phosphines and phosphites.

In one embodiment, the at least one reducing agent may be chosen from thioglycolic acid, cysteine, and derivatives thereof. In another embodiment, the reducing agent may be used in an aqueous solution.

When a thiol is being used as the reducing agent, for example, thioglycolic acid, the reducing agent may be used in a solution, in a concentration ranging from 0.05 to 1 M, the pH of the aqueous solution may range from 6.5 to 9, and the contacting time generally may range from 1 to 15 minutes, for example, from 5 to 10 minutes.

When a cysteine is being used as the reducing agent, the reducing agent may be used in a solution, in a concentration ranging from 0.01 to 9%, the pH of the aqueous solution may range from 6.5 to 10, and the contacting time may range from 1 to 15 minutes, for example, from 5 to 10 minutes.

The pH may be adjusted using an agent chosen, for example, from ammonia, monoethanolamine, diethanolamine, triethanolamine, 1,3-propanediamine, alkali carbonates, alkali bicarbonates, ammonium carbonates, ammonium bicarbonates, organic carbonates such as guanidine carbonate, alkali hydroxides, and quaternary ammonium hydroxides.

The at least one oxidizing agent may be chosen from hydrogen peroxide; oxygenated water; urea peroxide; alkaline metal bromates; persalts, for example, perborates and persulfates; and enzymes, for example, peroxidases and two electron oxydo-reductases.

As used herein, a fixing polymer refers to a polymer able to impart some shape to a given hair or able to maintain the hair in a given shape.

As used herein, a non crystalline fixing polymer refers to any polymer which does not comprise any crystallizable sequence in their structure, and, therefore, being free of any temperature change of the first order solid-liquid phase.

As used herein, a non crystalline or semi-crystalline fixing polymer refers to cationic, anionic, amphoteric, or non ionic fixing polymers.

Examples of cationic fixing polymers include, but are not limited to, polymers comprising primary, secondary, tertiary, and/or quaternary amine groups belonging to the polymeric chain or directly linked to the same, and having a molecular weight ranging from 500 to about 5,000,000 for example, from 1,000 to 3,000,000.

Such polymers may include, for example:

(1) homopolymers or copolymers derived from acrylic or methacrylic esters and amides and comprising at least one pattern chosen from:

wherein:

$R_a$ and $R_b$, which may be identical or different, are chosen from hydrogen and $C_{1-6}$ alkyl groups, hd c is chosen from hydrogen and $CH_3$, $R_d$, $R_e$, and $R_f$, which may be identical or different, are chosen from $C_{1-18}$ alkyl and benzyl groups, A is chosen from linear or branched $C_{1-6}$ alkyl groups and linear or branched $C_{1-4}$ hydroxyalkyl groups, and $X^-$ is chosen from methosulfate and halogenide anions such as a chloride and bromide.

The copolymers of family (1) may additionally comprise at least one pattern derived from comonomers optionally chosen from the acrylamide, methacrylamide, diacetone-acrylamide, acrylamide, and methacrylamide families, substituted on the nitrogen by at least one entity chosen from lower alkyl groups, acrylic or methacrylic acids, and the esters thereof, vinyllactams such as vinylpyrrolidone and vinylcaprolactam, and vinyl esters.

Non-limiting examples of copolymers of family (1) may thus include:

acrylamide and methacrylate dimethylaminoethyl copolymers quaternized with dimethyl sulfate or with a dimethyl halogenide, such as that sold under the designation HERCOFLOC® by HERCULES, acrylamide and methacryloyl-oxyethyltrimethylammonium chloride copolymers disclosed, for example, in European Patent Application No. 0 080 976 and marketed under the designation BINA QUAT® P 100 by CIBA GEIGY, acrylamide and methacryloyloxyethyltrimethylammonium methosulfate copolymers such as that marketed under the designation RETEN® by HERCULES, vinylpyrrolidone/dialkylaminoalkyl acrylate or methacrylate copolymers, which may be optionally quaternized, such as the products marketed under the designation GAFQUAT® by ISP, for example, GAF-QUAT® 734 and GAFQUAT® 755, as well as the products marketed as COPOLYMER® 845, 958, and 937. Those polymers are described, for example, in French Patent Application Nos. 2 077 143 and 2 393 573, dimethyl-aminoethyl methacrylate/vinylcaprolactame/vinylpyrrolidone terpolymers such as the product marketed under the designation GAFFIX VC 713 by ISP, and quaternized vinylpyrrolidone/dimethylaminopropyl methacrylamide copolymer such as the product marketed under the designation GAFQUAT® HS 100 by ISP.

(2) Quaternized polysaccharides disclosed, for example, in U.S. Pat. Nos. 3,589,578 and 4,031,307 such as guar gums containing cationic trialkylammonium groups.

Such products are marketed, for example, under the commercial designations JAGUAR® C13 S, JAGUAR® C15, and JAGUAR® C17 by MEYHALL.

(3) Vinylpyrrolidone and vinylimidazole quaternary copolymers such as the products marketed by BASF under the designation LUVIQUAT® TFC, (4) chitosans and the salts thereof, for example, chitosan acetate, lactate, glutamate, gluconate, and pyrrolidonecarboxylate.

Examples of chitosans and salts thereof include, but are not limited to, the chitosan with a deacetylation rate of 90.5% by weight marketed, for example, under the designation KYTAN BRUT STANDARD® by ABER TECHNOLOGIES, and the chitosan pyrrolidonecarboxylate, marketed, for example, under the designation KYTAMER® PC by the MERCHOL company.

(5) Cationic cellulose derivatives such as cellulose copolymers or cellulose derivatives grafted with a water-soluble monomer comprising a quaternary ammonium group and disclosed, for example, in U.S. Pat. No. 4,131,576, such as hydroxyalkylcelluloses, for example, hydroxymethylhydroxyethyl- and hydroxypropylcelluloses, for instance, grafted with a salt chosen from methacryloyloxyethyltrimethylammonium, methacrylamidopropyltrimethylammonium, and dimethyidiallylammonium salts.

The marketed products corresponding to such a definition include, for example, the products marketed under the designations CELQUAT® L 200 and CELQUAT® H 100 by NATIONAL STARCH.

Non-limiting examples of suitable anionic fixing polymers include polymers comprising groups derived from carboxylic, sulfonic, or phosphoric acids, and having a weight average molecular weight ranging from 500 to 5,000,000.

The carboxylic acid groups may be provided by unsaturated monomers containing one or two carboxylic acid functions, such as those of formula (I):

wherein n is an integer ranging from 0 to 10,

A is a methylene, optionally linked to the carbon atom of the unsaturated group or the adjacent methylene group, when n is greater than 1, via a heteroatom such as oxygen or sulfur, $R_3$ is chosen from hydrogen and phenyl and benzyl radicals, $R_1$ is chosen from hydrogen, lower alkyl radicals, and lower carboxyl radicals, and $R_2$ is chosen from hydrogen and lower alkyl, —$CH_2$—COOH, phenyl, and benzyl radicals.

In formula (I), in at least one embodiment, a lower alkyl radical may represent a group comprising from 1 to 4 carbon atoms, for example, a methyl or ethyl radical.

According to one embodiment of the present disclosure, the carboxylated anionic fixing polymers may be chosen from:

A) homo- or copolymers of acrylic or methacrylic acid and the salts thereof, for example, the products marketed under the names VERSICOL® E and K by ALLIED COLLOID and under the name ULTRAHOLD® by BASF; the acrylic acid and acrylamide copolymers marketed as a sodium salt under the names RETEN 421, 423, and 425 by HERCULES; and the sodium salts of polyhydroxycarboxylic acids;

B) acrylic acid or methacrylic acid and monoethylene monomer copolymers, such as ethylene, styrene, vinyl esters, acrylic, and methacrylic acid esters.

Such copolymers may be grafted on a polyalkylene glycol such as polyethyleneglycol and may be optionally crosslinked.

Such polymers are discussed, for example, in French Patent Application No. 1 222 944 and German Patent Application No. 23 30 956. Additional examples include copolymers comprising in their chain an optionally N-alkylated and/or hydroxyalkylated acrylamide pattern, such as those disclosed in Luxembourg Patent Nos. 75370 and 75371, or marketed under the name QUADRAMER® by AMERICAN CYANAMID.

Further examples include, but are not limited to, acrylic acid and $C_1$-$C_4$ alkyl methacrylate copolymers, terpolymers of vinylpyrrolidone, (meth)acrylic acid, and $C_1$-$C_{20}$ alkyl (meth)acrylate, for example, lauryl (ACRYLDONE LM from ISP), tert-butyl (LUVIFLEX VBM 70 marketed by BASF), and methyl (STEPANHOLD EXTRA marketed by STEPAN), and terpolymers of methacrylic acid/ethyl acrylate/tert-butyl acrylate such as the product marketed under the designation LUVIMER 100 P by BASF company.

C) Copolymers derived from crotonic acid, such as those comprising in their chain vinyl acetate or propionate patterns and optionally other monomers such as allyl, methallyl, and vinyl esters of a saturated, linear or branched carboxylic acid, with a long hydrocarbon chain comprising at least 5 carbon atoms, such polymers being optionally grafted or cross-linked, and the vinyl, allyl, and methallyl esters of a carboxylic α- or β-cyclic acid.

Such polymers are disclosed, for example, in French Patent Application Nos. 1 222 944, 1 580 545, 2 265 782, 2 265 781, 1 564 110, and 2 439 798.

Examples of commercial products include, but are not limited to, 28-29-30, 26-13-14, and 28-13-10 resins marketed by NATIONAL STARCH.

D) Copolymers derived from $C_4$-$C_8$ mono-unsaturated carboxylic acids or anhydrides, chosen from:

copolymers comprising:
i. at least one entity chosen from maleic, fumaric, and itaconic acids and anhydrides and
ii. at least one monomer chosen from vinyl esters, vinyl ethers, vinyl halogenides, phenylvinyl derivatives, and acrylic acid and the esters thereof, the anhydride functions of such copolymers being optionally monoesterified or monoamidified.

Such polymers are discussed, for example, in U.S. Pat. Nos. 2,047,398, 2,723,248, and 2,102,113 and British Patent No. 839,805, for example, those marketed under the designations GANTREZ AN and ES, and AVANTAGE® CP by ISP.

copolymers comprising (i) at least one entity chosen from maleic, citraconic, and itaconic anhydrides and (ii) at least one monomer chosen from allyl or methallyl esters optionally comprising at least one group chosen from acrylamide, methacrylamide, and α-olefin groups, acrylic or methacrylic esters, acrylic or methacrylic acids, and vinylpyrrolidone in their chain, the anhydride functions of such copolymers being optionally monoesterified or monoamidified.

Such polymers are discussed, for example, in French Patent Application Nos. 2 350 384 and 2 357 241.

E) polyacrylamides comprising carboxylate groups.

The anionic groups of the anionic fixing polymers of the present disclosure may also be chosen from sulfonic acid groups provided by patterns chosen from vinylsulfonic, styrenesulfonic, naphthalenesulfonic, and acrylamidoalkylsulfonic patterns.

Such polymers with sulfonic acid groups may be chosen, for example, from:
poly(vinylsulfonic acid) salts with a weight average molecular weight ranging from 1,000 to 100,000 and copolymers of vinylsulfonic acid and unsaturated comonomers such as acrylic acid, methacrylic acid, and the esters of said acids; acrylamide; acrylamide derivatives; vinyl ethers; and vinylpyrrolidone;
poly(styrenesulfonic) acid salts. Examples of such salts include, but are not limited to, sodium salts with a weight average molecular weight ranging from about 500,000 to about 100,000, marketed, for instance, under the designations FLEXAN® 500 and FLEXAN® 130 by NATIONAL STARCH. Such compounds are disclosed, for example, in the French Patent No. 2 198 719;
salts of poly(acrylamidesulfonic) acid, such as those disclosed in U.S. Pat. No. 4,128,631, for example, the poly (acrylamidoethyl-propanesulfonic) acid marketed under the designation COSMEDIA POLYMER® HSP 1180 by HENKEL.

According to one embodiment of the present disclosure, the anionic fixing polymers may be chosen from acrylic acid copolymers, such as acrylic acid/ethyl acrylate/N-tertiobutylacrylamide terpolymers marketed, for example, under the designation ULTRAHOLD STRONG by BASF, copolymers derived from crotonic acids such as vinyl acetate/vinyl tert-butyl benzoate/crotonic acid terpolymers and crotonic acid/ vinyl acetate/vinyl neododecanoate terpolymers marketed, for example, under the designation 28-29-30 Resin by NATIONAL STARCH, copolymers derived from an entity chosen from maleic, fumaric, and itaconic acids and anhydrides and comprising, as comonomers, vinyl esters, vinyl ethers, vinyl halogenides, phenylvinyl derivatives, acrylic acid and esters of acrylic acid, such as methylvinylether/ monoesterified maleic anhydride, marketed, for example, under the designation GANTREZ by ISP, methyl methacrylate acid copolymers marketed, for instance, under the designation EUDRAGIT-L by ROHM PHARMA, methacrylic acid/methyl methacrylate/$C_{1-4}$ alkyl acrylate/acrylic acid or $C_{1-4}$ hydroxyalkyl methacrylate, marketed, for example, under the designation AMERHOLD DR 25 by AMERCHOL and under the designation ACUDYNE 255 by ROHM & HAAS, methacrylic acid and ethyl acrylate copolymers marketed, for instance, under the designation LUVIMER MAEX and MAE by BASF and vinyl acetate/crotonic acid copolymers and vinyl acetate/crotonic acid copolymers grafted by polyethyleneglycol marketed, for example, under the designation ARISTOFLEX A by BASF.

Amphoteric fixing polymers useful in accordance with the present disclosure may include, for example, polymers comprising B and C patterns statistically distributed in the polymeric chain, wherein B is a pattern derived from a monomer comprising at least one basic nitrogen atom and C is a pattern derived from a monomer comprising at least one group chosen from carboxylic acid and sulfonic acid groups. The amphoteric fixing polymers may also optionally comprise zwitterionic patterns chosen from carboxybetaine and sulfobetaine pattern types. The amphoteric fixing polymers may also be chosen from polymers with a main cationic chain comprising primary, secondary, tertiary, and/or quaternary amine groups, amongst which at least one of them bears, through a hydrocarbon moiety, at least one group chosen from carboxylic acid and sulfonic acid groups. The amphoteric fixing polymers may also optionally have an anionic chain derived from unsaturated dicarboxylic acids, one carbonyl group of which being led to react with a polyamine comprising at least one group chosen from primary and secondary amine groups.

In at least one embodiment, the amphoteric fixing polymers may be chosen, for example, from:
1. polymers resulting from the copolymerization of a vinyl monomer bearing a carboxylic acid group, such as acrylic acid, methacrylic acid, maleic acid, and chloroacrylic acid, and a vinyl monomer containing at least one basic function, such as dialkylaminoalkyl methacrylate and acrylate, and dialkylaminoalkyl(meth)acrylamides. Such compounds are disclosed, for example, in U.S. Pat. No. 3,836,537;
2. polymers comprising patterns derived from:
   (a) at least one monomer chosen from N-alkylated acrylamides and methacrylamides,
   (b) at least one comonomer comprising at least one carboxylic acid function, and
   (c) at least one basic comonomer, such as esters with primary, secondary, tertiary, and/or quaternary amine substituents of acrylic acid and methacrylic acid, and the quaternization product of dimethylaminoethyl methacrylate with dimethyl or diethyl sulfate.

Non-limiting examples of N-alkylated acrylamides and methacrylamides (a) include those with $C_{2-12}$ alkyl moieties, such as N-ethylacrylamide, N-tert-butylacrylamide, N-tert-octylacrylamide, N-octylacrylamide, N-decylacrylamide, N-dodecylacrylamide, and the corresponding methacrylamides.

Suitable carboxylic acid group comonomers (b) may be chosen, for example, from acrylic, methacrylic, crotonic, itaconic, maleic, and fumaric acids and $C_{1-4}$ alkyl monoesters of maleic and fumaric acids and anhydrides.

Examples of basic comonomers (c) include, but are not limited to, aminoethyl methacrylate, butylaminoethyl methacrylate, N,N'-dimethylaminoethyl methacrylate, and N-tertiobutylaminoethyl methacrylate.

Further examples of copolymers include those having the CTFA designation ($4^{th}$ Ed., 1991) the "Octylacrylamide/acrylates/butylamino-ethylmethacrylate copolymer", such as the products marketed under the designation AMPHOMER® and LOVOCRYL® 47 by NATIONAL STARCH.

(3) Cross-linked and alkylated polyaminoamides, partially or completely derived from polyaminoamides of formula (II):

$$—[C(=O)—R_4—C(=O)—Z-]—\quad\quad (II)$$

wherein $R_4$ is a divalent moiety derived from an entity chosen from saturated dicarboxylic acid, mono- and dicarboxylic acids with a double ethylene link, $C_{1-6}$ alkyl esters of such acids, and moieties derived from the addition of any of said acids on a bis primary or bis secondary amine, and Z is a moiety of a bis-primary, mono- or bis-secondary polyalkylene polyamine, and, in at least one embodiment, may be:

(a) in an amount ranging from 60 to 100 mole %, the moiety of formula (III):

$$—NH—[(CH_2)_x—NH]_p—\quad\quad (III)$$

wherein x=1 and p=2 or 3, or alternatively, x=3 and p=2, such a moiety being derived from diethylenetriamine, triethylenetetraamine, or dipropylenetriamine;

(b) in an amount ranging from 0 to 40 mole %, the moiety of formula (III), wherein x=2 and p=1, derived from ethylenediamine, or the moiety:

$$—N\underset{\phantom{.}}{\diagdown}\underset{\phantom{.}}{\diagup}N—$$

derived from piperazine:

(c) in an amount ranging from 0 to 20 mole %, the moiety —NH—$(CH_2)_6$—NH— derived from hexamethylenediamine, such polyaminoamines being cross-linked through adding 0.025 to 0.35 mole per mole of amine group, a bifunctional cross-linking agent chosen from epihalohydrines, diepoxides, dianhydrides, diunsaturated compounds, and alkylated by acrylic acid, chloracetic acid, or an alkane-sulfone.

The saturated carboxylic acids may be chosen from acids comprising from 6 to 10 carbon atoms, such as adipic acid, trimethyl-2,2-4-adipic acid, trimethyl-2,4,4-adipic acid, terephthalic acid, and double ethylene linked acids, for example, acrylic, methacrylic, and itaconic acids.

In at least one embodiment, the alkane-sulfones used in the alkylation may be chosen from propanesulfone and butanesulfone.

Salts of the alkylation agents may be chosen, for example, from sodium and potassium salts.

(4) Polymers comprising zwitterionic patterns of formula (IV):

$$R_5{-\!\!\left[\begin{array}{c}R_6\\|\\C\\|\\R_7\end{array}\!-\!\begin{array}{c}R_8\\|\\N^+\\|\\R_9\end{array}\!-\!(CH_2)_z\!-\!\overset{O}{\underset{\|}{C}}\!-\!O^-\right]_y}\quad (IV)$$

wherein $R_5$ is a polymerizable unsaturated group chosen, for example, from acrylate, methacrylate, acrylamide, and methacrylamide groups, y and z, which may be identical or different, are integers ranging from 1 to 3, $R_6$ and $R_7$, which may be identical or different, are chosen from hydrogen and methyl, ethyl, and propyl groups, and $R_8$ and $R_9$, which may be identical or different, are chosen from hydrogen and alkyl moieties, wherein the total number of carbon atoms in $R_8$ and $R_9$ is not higher than 10.

Polymers comprising such patterns with formula (IV) may optionally further comprise patterns derived from non zwitterionic monomers such as dimethyl and diethylaminoethyl acrylate and methacrylates, alkyl acrylates and methacrylates, acrylamides and methacrylamides, and vinyl acetate.

A non-limiting example of such a polymer is methyl methacrylate/dimethylcarboxy-methylammonioethyl methacrylate copolymer, such as the product marketed under the designation DIAFORMER® Z301 by SANDOZ.

(5) Polymers derived from chitosan comprising monomeric patterns chosen from those of formulae (V)-(VII):

(V) — chitosan unit with $CH_2OH$, OH, and NHCOCH$_3$ substituents (VI) — chitosan unit with $CH_2OH$, OH, and NH$_2$ substituents (VII) — chitosan unit with $CH_2OH$, OH, and NH—C(=O)—$R_{10}$—COOH substituents wherein the pattern of formula (V) is present in an amount ranging from 0 to 30%, the pattern of formula (VI) is present in an amount ranging from 5 to 50%, and the pattern of formula (VII) is present in an amount ranging from 30 to 90%, provided that in such a pattern (VII), $R_{10}$ is a moiety of formula (VIII):

(VIII)

wherein:

if q=0, then $R_1$, $R_{12}$, and $R_{13}$, which may be identical or different, are chosen from hydrogen, methyl groups, hydroxyl groups, acetoxy groups, amino groups, monoalkylamine groups, dialkylamine group optionally interrupted by at least one nitrogen atom and/or optionally substituted by at least one group chosen from amine, hydroxyl, carboxyl, alkylthio, and sulfo groups, alkylthio groups with the alkyl group bearing an amino residue, in such a case at least one of the moieties $R_{11}$, $R_{12}$, and $R_{13}$ being a hydrogen atom; or if q=1, then $R_{11}$, $R_{12}$, and $R_{13}$ are hydrogen, as well as the acid and base addition salts of such compounds.

6) Polymers obtained through N-carboxyalkylation of chitosan, such as N-carboxymethylchitosan and N-carboxybutylchitosan marketed under the designation EVALSAN® by JAN DEKKER.

(7) Polymers comprising recurrent units of formula (IX):

(IX)

disclosed, for example, in French Patent Application No. 1,400,366, wherein $R_{14}$ is chosen from hydrogen, $CH_3O$, $CH_3CH_2O$, and phenyl moieties, $R_{15}$ is chosen from hydrogen and lower alkyl moieties such as methyl and ethyl moieties, $R_{16}$ is chosen from hydrogen and lower alkyl moieties such as methyl and ethyl moieties, $R_{17}$ is chosen from lower alkyl moieties such as methyl and ethyl moieties, and moieties of formula:

—$R_{18}$—$N(R_{16})_2$, wherein $R_{18}$ is chosen from —$CH_2$—$CH_2$—, —$CH_2$—$CH_2$—$CH_2$—, an —$CH_2$—$CH(CH_3)$— groups and $R_{16}$ is defined as above, as well as the higher homologues of such moieties comprising up to 6 carbon atoms.

(8) Amphoteric polymers of the -D-X-D-X-type chosen from:

(a) polymers obtained by the action of chloroacetic acid or sodium chloroacetate on compounds comprising at least one pattern of formula (X):

-D-X-D-X-D-     (X)

wherein D is a moiety of formula:

and X is chosen from the symbols E and E', wherein E and E', which may be identical or different, are chosen from bivalent moieties, such as alkylene moieties with a straight or a branched chain comprising up to 7 carbon atoms in the main non-substituted chain, or substituted by hydroxyl groups, and optionally comprising, in addition to oxygen, nitrogen, and/or sulfur atoms, 1 to 3 aromatic and/or heterocyclic rings, the oxygen, nitrogen, and sulfur atoms being present as groups chosen from ether, thioether, sulfoxide, sulfone, sulfonium, alkylamine, alkenylamine groups, hydroxyl, benzylamine, amine oxide, quaternary ammonium, amide, imide, alcohol, ester, and/or urethane groups.

b) Polymers of formula (X'):

-D-X'-D-X'-     (X')

wherein D is a moiety of formula:

and X' is chosen from the symbols E and E'', and at least once E'', wherein E is defined as above and E'' is chosen from bivalent moieties, such as straight or branched chain alkylene moieties, having up to 7 carbon atoms in the main chain, optionally substituted by at least one moiety, and comprising at least one nitrogen atom, the nitrogen atom being substituted by an alkyl chain optionally interrupted by an oxygen atom and comprising at least one function chosen from carboxyl functions and hydroxyl functions and betainized through reaction with chloroacetic acid or soda chloroacetate.

9) $(C_{1-5})$alkyl vinylether/maleic anhydride copolymers partially modified by semi-amidation with an N,N-dialkylaminoalkylamine such as N,N-dimethylaminopropylamine, or by semi-esterification with an N,N-dialkanolamine. Such copolymers may also comprise other vinyl comonomers such as vinylcaprolactam.

In one embodiment, the amphoteric fixing polymers may be chosen from those of family (3), such as those with the CTFA designation being "Octylacrylamide/acrylates/butylaminoethyl-methacrylate copolymer". Other examples include products marketed under the designations ®AMPHOMER® LV 71 and LOVOCRYL® 47 by NATIONAL STARCH.

In another embodiment, the amphoteric fixing polymers may be chosen from those of family (4), for example, methyl methacrylate and dimethylcarboxymethyl-ammonioethyl methacrylate copolymers, marketed, for example, under the designation DIAFORMER® Z301 by SANDOZ.

The anionic or amphoteric fixing polymers may, as needed, be partially or fully neutralized. Neutralization agents may include, for example, soda, potassium hydroxide, amino-2-methylpropanol, monoethanolamine, triethanolamine, tri-isopropanolamine, and mineral or organic acids such as hydrochloric acid or citric acid.

Non ionic fixing polymers which may be used in accordance with the present disclosure may be chosen, for example, from:

vinylpyrrolidone homopolymers, vinylpyrrolidone and vinyl acetate copolymers, polyalkyloxazolines, such as the polyethyloxazolines marketed by DOW CHEMICAL under the designations PEOX® 50 000, PEOX® 200 000, and PEOX® 500 000, vinyl acetate homopolymers, such as the product marketed under the designation APPRETAN® EM by HOECHST and under the name RHODOPAS® A 012 by RHONE POULENC, vinyl acetate and acrylic ester copolymers, such as the product marketed under the designation RHODOPAS® AD 310 by RHONE POULENC, vinyl acetate and ethylene copolymers, such as the product marketed under the name APPRETAN® TV by HOECHST, vinyl acetate and maleic ester copolymers, for example, dibutyl maleate copolymers, such as the product marketed under the name APPRETAN® MB EXTRA by HOECHST, ethylene and maleic anhydride copolymers, alkyl acrylate and alkyl methacrylate homopolymers such as the product marketed under the designation MICROPEARL® RQ 750 by MATSUMOTO or the product marketed under the designation LUHYDRAN® A 848 S by BASF, acrylic ester copolymers such as, for example, alkyl acrylate and alkyl methacrylate copolymers such as the products marketed by ROHM & HMS under the designations PRIMAL AC-261 K and EUDRAGIT NE 30 D, by BASF under the designations ACRONAL 601, LUHYDRAN LR 8833 and 8845, and by HOECHST under the designations APPRETAN N 9213 and N 9212, copolymers of acrylonitrile and a non ionic monomer chosen, for example, from butadiene and alkyl (meth)acrylates; for instance, the products marketed under the designations NIPOL® LX 531 B by NIPPON ZEON and those marketed under the designation CJ 0610 B by ROHM & HAAS, polyurethanes such as the products marketed under the designations ACRYSOL® RM 1020 and ACRYSOL® RM 2020 by ROHM & HMS, the products URAFLEX® XP 401 UZ, URAFLEX® XP, and 402 UZ by DSM RESINS, alkyl acrylate and urethane copolymers such as the 8538-33 product marketed by NATIONAL STARCH, polyamides such as the ESTAPOR® LO 11 product marketed by RHONE POULENC, and chemically modified or non modified non ionic guars.

Non modified non ionic guars may include, for example, the products sold under the designation VIDOGUM® GH 175 by UNIPECTINE and under the JAGUAR® C designation by MEYHALL. Modified non ionic guars suitable for use in accordance with the present disclosure may include, for example, $C_{1-8}$ hydroxyl groups, such as hydroxymethyl, hydroxyethyl, hydroxypropyl, and hydroxybutyl groups.

Such guars are well known in the art and may be, for example, prepared through reaction of the corresponding alkene oxides, for example, propylene oxides, with the guar so as to obtain a guar modified by hydroxypropyl groups.

Such non ionic guars optionally modified by hydroxyl groups may include, for example, those marketed under the designations JAGUAR® HP8, JAGUAR® HP60, JAGUAR® HP120, JAGUAR® DC 293, and JAGUAR® HP 105® by MEYHALL or under the designation GALACTASOL 4H4FD2 by AQUALON.

In accordance with one embodiment of the present disclosure, further examples of fixing polymers may include film-forming polymers of the grafted silicone type comprising a polysiloxane part and a part comprising a non silicone organic chain, one of both parts comprising the main chain of the polymer and the other part being grafted on said main chain.

Such polymers are discussed, for example, in European Patent Application Nos. 0 412 704, 0 412 707, 0 640 105, and 0 582 152, International Patent Application Publication Nos. WO 95/00578 and WO 93/23009, and U.S. Pat. Nos. 4,693,935, 4,728,571, and 4,972,037.

Such polymers may be, in at least one embodiment, chosen from anionic and non ionic polymers.

Such polymers may include, for example, copolymers able to be obtained through radical polymerization from the monomer mixture formed with:

a) from 50 to 90% by weight of tert-butyl acrylate,
b) from 0 to 40% by weight of acrylic acid,
c) from 5 to 40% by weight of a silicone macromer with the formula:

wherein v is an integer ranging from 5 to 700, the percentages by weight calculated based on the total weight of the monomers.

Other examples of grafted silicone polymers may include, for example, polydimethylsiloxanes (PDMS) onto which are grafted, through a linking chain of the thiopropylene type, mixed polymeric patterns of the poly(meth)acrylic acid type and of the alkyl poly(meth)acrylate type and polydimethylsiloxanes (PDMS) onto which are grafted, through a linking chain of the thiopropylene type, polymeric patterns of the isobutyl poly(meth)acrylate.

In at least one embodiment, polyurethanes may also be used as fixing polymers, which may be optionally functionalized, and optionally of the silicone type or not.

Examples of suitable polyurethanes in accordance with the present disclosure include those disclosed in European Patent Application Nos. 0 751 162, 0 637 600, 0 648 485, 0 656 021, and 0 619 111, French Patent Application No. 2,743,297, and International Patent Application Publication No. WO 94/03510.

Cerids are fatty acid and aliphatic alcohols monoesters with a long chain. In at least one embodiment, such aliphatic alcohols may be primary alcohols with an even number of saturated and non branched carbons. The length of the carbon chain may range from 14 to 30 atoms for the fatty acid, and from 16 to 36 carbon atoms for the fatty alcohol. Non-limiting examples of cerids include cetyl palmitate, ceryl palmitate, and myricyl palmitate.

Cerids are important constitutive elements of animal or plant waxes. In at least one embodiment, plant waxes may be used as cerid sources for the compositions according to the disclosure, for example, carnauba wax, candelilla wax, and beeswax.

Sterids are obtained through the esterification of fatty acids by sterols. Examples of sterols may include cholesterol, ergosterol, lanosterol, agnosterol, stigmasterol, and fucosterol. The fatty acids may, in at least one embodiment, comprise from 14 to 30 carbon atoms. A non-limiting example of a suitable sterid is cholesteryl, palmitate. A non-limiting example of a sterid source is lanoline.

In one embodiment, the active ingredient present in the cosmetic composition according to the disclosure may be a fixing polymer.

In another embodiment of the present disclosure, the cosmetic composition, comprising at least one non crystalline or semi-crystalline fixing polymer may also comprise a compound chosen from silicones in a soluble, dispersed, micro, or nano dispersed form, whether volatile or not volatile; thickeners; non ionic, anionic, cationic, and amphoteric surfactants; conditioners; suds suppressors; moisturizing agents; emollient agents; plasticizers; silicone or non-silicone water-soluble and fat-soluble sunscreens; permanent or temporary dyes; colored or non-colored mineral or organic pigments; mineral fillers; clays; pearlescent agents, opacifying agents; colloidal agents; perfumes; peptizers; preservatives; ceramids; pseudo-ceramids; vitamins; provitamins including panthenol; proteins; sequestrants; solubilizers; alkanizing agents; anti-corrosion agents; fatty substances other than cerids and sterids, such as vegetal, animal, mineral, and synthetic oils; and mixtures thereof.

In at least one embodiment, the above described cosmetic composition may be a liquid composition comprising a physiologically acceptable solvent comprising water and/or at least one organic solvent.

The at least one organic solvent may be chosen from water, $C_1$ to $C_4$ lower alcohols such as ethanol, isopropanol, acetone, methylethylcetone, ethyl acetate, methyl acetate, butyl acetate, diethoxyethane, dimethoxyethane, $C_6$ to $C_{10}$ alkanes, and mixtures thereof.

The at least one non crystalline or semi-crystalline fixing polymer, and/or at least one cerid, and/or at least one sterid may be present in the cosmetic composition in an amount ranging from 0.1 to 30% by weight relative to the total weight of the cosmetic composition, for example, from 0.5 to 20% by weight.

The composition may further comprise at least one cosmetic builder, which may be present in the cosmetic composition in an amount ranging from 0.0001 to 40% by weight relative to the total weight of the cosmetic composition, for example, from 0.001 to 20% by weight.

The cosmetic composition disclosed herein may also be used in a method for durably modifying the shape of the hair.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLE

The following compositions were prepared:

| Composition A | |
|---|---|
| Polyurethane[1] (1) | 5.0% MA |
| Perfume | 0.4% |
| Water | 94.6% |
| Composition B | |
| Microdispersion of carnauba wax | 26 g (either 7% MA, or 5.9% of cerids)[2] |
| Water | qs 100 g |
| Composition C | |
| Lanolin | 100% |

[1]Luviset Si Pur marketed by BASF
[2]MEROXYL SAP marketed by CHIMEX

Coating method

1. Locks of hair were coated with a thioglycolic acid solution (1 M, pH = 9, pH adjusted using ammonia). The thioglycolic acid was allowed to penetrate into the fiber core for 5 minutes.
2. The locks of hair were rinsed and optionally pre-dried.
3. The locks of hair were coated with the cosmetic composition A.
4. A waving tong was applied to the locks of hair so as to create waves. Alternatively, a curling tong may be applied to the locks of hair so as to form hair curls, or any other type of tong may be applied to the hair to impart a shape.
5. Subsequently, an oxygenated water solution with 8 vol. pH 3 (pH adjusted with citric acid) was applied to the locks of hair and allowed to stand for 5 minutes.
6. The locks of hair were rinsed and the cosmetic composition was removed.
7. The hair was able to maintain the shape even in the presence of a shampoo or a solvent.

The hair styles obtained had durable shapes: waves, curls, and waving locks, depending on the tongs being used. The same type of result was obtained using compositions B and C instead of composition A.

What is claimed is:

1. A method for imparting shape to keratinous fibers comprising:
   coating the keratinous fibers with a reducing agent,
   rinsing the keratinous fibers,
   coating the keratinous fibers with a cosmetic composition comprising at least one non crystalline or semi-crystalline fixing polymer, and at least one cerid, and at least one sterid,
   raising the temperature of the keratinous fibers using a heating tong, up to a temperature ranging from 50 to 280° C., and
   coating the keratinous fibers with an oxidizing agent.

2. The method of claim 1, wherein the at least one non crystalline or semi-crystalline fixing polymer is chosen from anionic, cationic, amphoteric, and non ionic fixing polymers.

3. The method of claim 1, wherein the heating tong is chosen from smoothing tongs, curling tongs, and waving tongs.

4. The method of claim 3, wherein the tongs comprise tweezers comprising two branches, each branch having a shape chosen from a rectangular shape, a curved shape, a triangular shape, and a polyhexagonal shape.

5. The method of claim 4, wherein the branches of the tweezers have a symmetrical shape or a shape complementary one relative to the other.

6. The method of claim 3, wherein the tongs comprise one single heating element around which keratinous fibers may be wound.

7. The method of claim 6, wherein said single heating element has a section with a shape chosen from circular, oval, square, rectangular, parallelepipedic, trapezoid, pentagonal, hexagonal, octagonal, and triangular shapes.

8. The method of claim 1, wherein the step for coating the keratinous fibers with a cosmetic composition comprising at least one non crystalline or semi-crystalline fixing polymer, and at least one cerid, and at least one sterid, and the step for raising the temperature of the keratinous fibers are carried out simultaneously.

9. The method of claim 1, wherein the reducing agent is chosen from: thiols chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and the esters and salts thereof; thioglycerol; cysteamine and the $C_1$-$C_4$ acylated derivatives thereof; N-mesylcysteamine; N-acetylcysteine; sugar N-mercaptoalkylamides chosen from N-(mercapto-2-ethyl) gluconamide, pantetheine, N-(mercaptoalkyl)-w-hydroxy alkylamides, N-mono or N,N-dialkylmercapto-4 butyramides, aminomercaptoalkylamides, derivatives of N-(mercapto-alkyl)succinamic acids, and N-(mercaptoalkyl)succinimides; alkylamino mercaptoalkylamides; the azeotropic mixture of 2-hydroxypropyl thioglycolate and (2-hydroxy-1-methyl) ethyl thioglycolate; N-mercaptoalkylalkane diamides, and mixtures thereof.

10. The method of claim 1, wherein the oxidizing agent is chosen from hydrogen peroxide, oxygenated water, urea peroxide, alkaline metal bromates, persalts, and enzymes.

11. The method of claim 10, wherein the persalts are chosen from perborates and persulfates.

12. The method of claim 10, wherein the enzymes are chosen from peroxidases and two electron oxydo-reductases.

13. The method of claim 1, wherein the at least one cerid is a mono ester of $C_{14}$ to $C_{30}$ fatty acids and $C_{16}$ to $C_{36}$ saturated and non branched saturated primary alcohols.

14. The method of claim 1, wherein the at least one cerid is obtained from carnauba wax, candelilla wax, or beeswax.

15. The method of claim 1, wherein the at least one sterid is an ester of $C_{14}$ to $C_{30}$ fatty acids and sterols.

16. The method of claim 1, wherein the at least one sterid is obtained from lanolin.

17. The method of claim 1, wherein said cosmetic composition further comprises a compound chosen from silicones in a soluble, dispersed, micro, or nano dispersed, volatile or non volatile form; thickeners; non ionic, anionic, cationic, and amphoteric surfactants; conditioners; softeners; suds suppressors; moisturizing agents; emollient agents; plasticizers; silicone or non-silicone water-soluble and fat-soluble sun screens; permanent or temporary dyes; colored or non-colored mineral or organic pigments; mineral fillers; clays; pearlescent agents; opacifiers; colloidal agents; perfumes; peptizers; preservatives; ceramids; pseudo-ceramids; vitamins; pro-vitamins; proteins; sequestrants; solubilizers; alkanizing agents; anti-corrosion agents; fatty substances other than cerids and sterids; and mixtures thereof.

18. The method of claim 1, wherein said cosmetic composition is a liquid composition comprising a physiologically acceptable solvent comprising water and/or at least one organic solvent.

19. The method of claim 18, wherein the at least one organic solvent is chosen from water, $C_1$ to $C_4$ lower alcohols, isopropanol, acetone, methylethylcetone, ethyl acetate, methyl acetate, butyl acetate, diethoxyethane, dimethoxyethane, $C_6$ to $C_{10}$ alkanes, and mixtures thereof.

20. The method of claim 1, wherein the at least one non crystalline or semi-crystalline fixing polymer, or the at least one cerid, or the at least one sterid is present in the cosmetic composition in an amount ranging from 0.1 to 30% by weight, relative to the total weight of the cosmetic composition.

21. The method of claim 20, wherein the at least one non crystalline or semi-crystalline fixing polymer, or the at least one cerid, or the at least one sterid is present in the cosmetic composition in an amount ranging from 0.5 to 20% by weight, relative to the total weight of the cosmetic composition.

22. The method of claim 1, further comprising at least one cosmetic builder, wherein the at least one cosmetic builder is present in the cosmetic composition in an amount ranging from 0.0001 to 40% by weight, relative to the total weight of the cosmetic composition.

23. The method of claim 22, wherein the at least one cosmetic builder is present in the cosmetic composition in an amount ranging from 0.001 to 20% by weight, relative to the total weight of the cosmetic composition.

* * * * *

UNITED STATES PATENT AND TRADEMARK OFFICE
CERTIFICATE OF CORRECTION

PATENT NO. : 7,815,901 B2
APPLICATION NO. : 11/340654
DATED : October 19, 2010
INVENTOR(S) : Estelle Mathonneau et al.

It is certified that error appears in the above-identified patent and that said Letters Patent is hereby corrected as shown below:

Claim 9, col. 17, line 28, "-w-hydroxy" should read "-ω-hydroxy"

Signed and Sealed this
Third Day of May, 2011

David J. Kappos
*Director of the United States Patent and Trademark Office*